(12) United States Patent
Murakami et al.

(10) Patent No.: US 12,329,832 B2
(45) Date of Patent: Jun. 17, 2025

(54) DENTAL POLYMERIZABLE COMPOSITION

(71) Applicant: GC Corporation, Shizuoka (JP)

(72) Inventors: Shogo Murakami, Tokyo (JP); Atsushi Fujimi, Tokyo (JP); Keita Sato, Tokyo (JP)

(73) Assignee: GC Corporation, Shizuoka (JP)

( * ) Notice: Subject to any disclaimer, the term of this patent is extended or adjusted under 35 U.S.C. 154(b) by 589 days.

(21) Appl. No.: 17/753,408

(22) PCT Filed: Aug. 28, 2020

(86) PCT No.: PCT/JP2020/032737
§ 371 (c)(1),
(2) Date: Mar. 2, 2022

(87) PCT Pub. No.: WO2021/049335
PCT Pub. Date: Mar. 18, 2021

(65) Prior Publication Data
US 2022/0296476 A1    Sep. 22, 2022

(30) Foreign Application Priority Data
Sep. 10, 2019 (JP) ................. 2019-164833

(51) Int. Cl.
| A61K 6/61 | (2020.01) |
| A61K 6/20 | (2020.01) |
| A61K 6/887 | (2020.01) |
| C08F 20/00 | (2006.01) |
| C08K 5/07 | (2006.01) |

(52) U.S. Cl.
CPC ........... *A61K 6/61* (2020.01); *A61K 6/20* (2020.01); *A61K 6/887* (2020.01); *C08F 20/00* (2013.01); *C08K 5/07* (2013.01)

(58) Field of Classification Search
CPC ......... C08F 20/00–40; C08F 22/00–24; C08F 120/00–40; C08F 122/00–24; C08F 220/00–40; C08F 222/00–24; C08K 5/07; C08L 33/00–12; A61K 6/00–90
See application file for complete search history.

(56) References Cited

U.S. PATENT DOCUMENTS

| 4,571,420 A * | 2/1986 | Marks ................. C08G 75/045 |
| | | 525/344 |
| 2012/0059083 A1 | 3/2012 | Tokui et al. |
| 2016/0051450 A1 | 2/2016 | Kashiki et al. |

FOREIGN PATENT DOCUMENTS

| EP | 2425808 | 3/2012 |
| EP | 2979681 | 2/2016 |
| EP | 3111914 | 1/2017 |
| JP | 2012-051856 | 3/2012 |
| WO | 2014/156077 | 10/2014 |

OTHER PUBLICATIONS

International Search Report for PCT/JP2020/032737 mailed on Nov. 10, 2020.

* cited by examiner

*Primary Examiner* — Kregg T Brooks
(74) *Attorney, Agent, or Firm* — IPUSA, PLLC

(57) ABSTRACT

A dental polymerizable composition includes a first agent containing a (meth)acrylate, a thiourea derivative, a vanadium compound, and a β-diketone, and a second agent containing a (meth)acrylate and an organic peroxide.

2 Claims, No Drawings

DENTAL POLYMERIZABLE COMPOSITION

TECHNICAL FIELD

The present invention relates to a dental polymerizable composition.

BACKGROUND ART

Dental cements are used in dental treatment when prostheses are worn.

In addition, dental polymerizable compositions other than dental cements, such as hypersensitivity protectors and sealants for children are used.

As an example of a dental polymerizable composition, a two-component dental polymerizable composition having a first agent containing an (meth)acrylate, a thiourea derivative, and a vanadium compound, and a second agent containing an (meth)acrylate and an organic peroxide is known (see, for example, Patent Document 1).

PRIOR ART DOCUMENTS

Patent Documents

[Patent Document 1] Japanese Patent Application Laid-Open No. 2012-51856

SUMMARY OF INVENTION

Problem to be Solved by the Invention

However, improving the curability after long-term storage of the two-component dental polymerizable composition has been desired. That is, improving the storage stability of the two-component dental polymerizable composition has been demanded.

One aspect of the invention is to provide a two-component dental polymerizable composition with excellent storage stability.

Means for Solving Problems

One aspect of the invention is a dental polymerizable composition including a first agent containing a (meth)acrylate, a thiourea derivative, a vanadium compound, and a β-diketone, and a second agent containing a (meth)acrylate and an organic peroxide.

Effects of the Invention

According to one embodiment of the present invention, the present invention provides a two-component dental polymerizable composition with excellent storage stability.

MODE FOR CARRYING OUT THE INVENTION

Next, embodiments for carrying out the present invention will be described.

[Dental Polymerizable Composition]

The dental polymerizable composition of the present embodiment is a two-component dental polymerizable composition including a first agent containing a (meth)acrylate, a thiourea derivative, a vanadium compound, and a β-diketone, and a second agent containing a (meth)acrylate and an organic peroxide.

Examples of the properties of the first agent and the second agent include a paste and the like.

A mass ratio of the first agent and the second agent in the dental polymerizable composition of the present embodiment is usually 10:1 to 1:10.

The dental polymerizable composition of the present embodiment is usually used by kneading the first agent and the second agent.

The dental polymerizable composition of the present embodiment can be applied to dental cements, protective agents for dentin sensitivities, pediatric sealants, and the like.

Hereinafter, components constituting the dental polymerizable composition of the present embodiment will be described.

[(meth)acrylate]

As used herein and in the claims, a (meth)acrylate refers to a compound having one or more (meth)acryloyloxy groups (for example, monomers, oligomers, prepolymers). In addition, (meth)acryloyloxy groups refer to methacryloyloxy groups and/or acryloyloxy groups.

Although the (meth)acrylate may or may not include an acid group, the dental polymerizable composition of the present embodiment preferably includes (meth)acrylate having an acid group. This can improve the adhesion of the dental polymerizable composition of the present embodiment.

Examples of (meth)acrylates having an acid group include (meth)acrylates having a phosphate group, (meth)acrylates having a pyrophosphate group, (meth)acrylates having a thiophosphate group, (meth)acrylates having a carboxyl group, (meth)acrylates having a sulfonic acid group, (meth)acrylates having a phosphonic acid group, and the like. Two or more of the (meth)acrylates may be used in combination. Among these, the (meth)acrylates having a phosphate group or a thiophosphate group are preferably used in terms of adhesion of the dental polymerizable composition of the present embodiment.

It should be noted that the (meth)acrylate having an acid group may have multiple acid groups.

Alternatively, acid chlorides, alkali metal salts, amine salts, and the like of (meth)acrylates having acid groups may be used instead of the (meth)acrylate having an acid group.

Examples of (meth)acrylates having a phosphate group include 2-(meth)acryloyloxyethyldihydrogenphosphate, bis[2-(meth)acryloyloxyethyl]hydrogenphosphate, 2-(meth)acryloyloxyethylphenyl hydrogenphosphate, 6-(meth)acryloyloxyhexyldihydrogenphosphate, 6-(meth)acryloyloxyhexylphenyl hydrogenphosphate, 10-(meth)acryloyloxydecyldihydrogenphosphate, 1,3-di(meth)acryloylpropane-2-dihydrogenphosphate, 1,3-di(meth)acryloylpropane-2-phenylhydrogenphosphate, bis[5-{2-(meth)acryloyloxyethoxycarbonyl}heptyl] hydrogenphosphate, and the like. Among these, 10-methacryloyloxydecyldihydrogenphosphate is preferably used in terms of adhesion of the dental polymerizable composition of the present embodiment.

Examples of (meth)acrylates having a pyrophosphate group include bis[2-(meth)acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, bis[10-(meth)acryloyloxydecyl] pyrophosphate, and the like.

Examples of (meth)acrylates having a thiophosphate group include 2-(meth)acryloyloxyethyldihydrogen thiophosphate, 3-(meth)acryloyloxypropyldihydrogen thiophosphate, 4-(meth)acryloyloxybutyldihydrogen thiophosphate, 5-(meth)acryloyloxypentyldihydrogen thiophosphate, 6-(meth)acryloyloxyhexyldihydrogen thiophosphate, 7-(meth)acryloyloxyheptyldihydrogen thiophosphate, 8-(meth)acryloyloxyoctyldihydrogen thiophosphate, 9-(meth)acryloyloxynonyldihydrogen thiophosphate, 10-(meth)acryloyloxydecyldihydrogen thiophosphate, 11-(meth)acryloyloxyundecyldihydrogen thiophosphate, 12-(meth)acryloyloxydodecyldihydrogen thiophosphate, 13-(meth)acryloyloxytridecyldihydrogen thiophosphate, 14-(meth)acryloyloxytetradecyldihydrogen thiophosphate, 15-(meth)acryloyloxypentadecyldihydrogen thiophosphate, 16-(meth)acryloyloxyhexadecyldihydrogen thiophosphate, 17-(meth)acryloyloxyheptadecyldihydrogen thiophosphate, 18-(meth)acryloyloxyoctadecyldihydrogen thiophosphate, 19-(meth)acryloyloxynonadecyldihydrogen thiophosphate, 20-(meth)acryloyloxyicosyldihydrogen thiophosphate, and the like.

Examples of (meth)acrylates having a carboxyl group include 4-(meth)acryloyloxyethyl trimellitic acid, 4-(meth)acryloyloxyethyl trimellitic anhydride, 4-(meth)acryloyloxy trimellitic acid, 4-(meth)acryloyloxydecyltrimellitic anhydride, 11-(meth)acryloyloxy-1,1-undecarboxylic acid, 1,4-di(meth)acryloyloxy pyromellitic acid, 2-(meth)acryloyloxyethylmaleic acid, 2-(meth)acryloyloxyethyl phthalic acid, 2-(meth)acryloyloxyethyl hexahydrophthalic acid, and the like.

Examples of (meth)acrylates having a sulfonic acid group include 2-(meth)acrylamide-2-methylpropanesulfonic acid, styrenesulfonic acid, 2-sulfoethyl (meth)acrylate, and the like.

Examples of (meth)acrylates having a phosphonic acid group include 2-(meth)acryloyloxyethylphenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and the like.

The content of the (meth)acrylate having an acid group in the dental polymerizable composition of the embodiment is preferably 0.1% by mass or more and 20% by mass or less, and further preferably 0.5% by mass or more and 10% by mass or less. If the content of the (meth)acrylate having an acid group in the dental polymerizable composition of the present embodiment is 0.1% by mass or more, the adhesion of the dental polymerizable composition of the present embodiment is further improved. If the content is 20% by mass or less, the curability of the dental polymerizable composition of the present embodiment is further improved.

Examples of the (meth)acrylates not having an acid group include methyl (meth)acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, 2-ethoxyethyl (meth)acrylate, 2-methylhexyl (meth)acrylate, 2-ethylhexyl (meth)acrylate, benzyl (meth)acrylate 2-hydroxy-1,3-di(meth)acryloyloxypropane, ethyleneglycol di(meth)acrylate, diethyleneglycol di(meth)acrylate, triethyleneglycol di(meth)acrylate, butyleneglycol di(meth)acrylate, neopentylglycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylol ethanetri(meth)acrylate, pentaerythritol tri(meth)acrylate, trimethylolmethacrylate (meth)acrylate, pentaerythritol tetra(meth)acrylate, polybutyleneglycol di(meth)acrylate, bisphenol A diglycidyl(meth)acrylate, di-2-(meth)acryloyloxyethyl-2,2,4-trimethylhexamethylene dicarbamate, 1,3,5-tris[1,3-bis{(meth)acryloyloxy}-2-propoxycarbonylaminohexane]-1,3,5-(1H,3H,5H)triazine-2,4,6-trione, 2,2-bis[4-(3-(meth)acryloyloxy-2-hydroxypropyl)phenyl]propane, N,N'-(2,2,4-trimethylhexamethylene)bis[2-(aminocarboxy)propane-1,3-diol]tetramethacrylate, and the like. Two or more of the (meth)acrylates not having an acid group may be used in combination. Among these, di-2-(meth)acryloyloxyethyl-2,2,4-trimethylhexamethylene dicarbamate, and 2-hydroxy-1,3-di(meth)acryloyloxypropane are preferably used in terms of the mechanical strength of the cured product of the dental polymerizable composition of the present embodiment.

The content of the (meth)acrylate not having an acid group in the dental polymerizable composition of the present embodiment is preferably 10% by mass or more and 95% by mass or less, and further preferably 15% by mass or more and 80% by mass or less. If the content of the (meth)acrylate not having an acid group in the dental polymerizable composition of the present embodiment is in the range of 10% by mass or more and 95% by mass or less, the workability of the dental polymerizable composition of the present embodiment is further improved.

[Organic Peroxides]

An organic peroxide functions as an oxidizing agent for a chemical polymerization initiator.

Examples of the organic peroxides include benzoyl peroxide, cumene hydroperoxide, t-butyl hydroperoxide, t-amyl hydroperoxide, 1,1,3,3-tetramethylbutyl hydroperoxide, 2,5-dimethyl-2,5-di(hydroperoxy)hexane, p-diisopropylbenzene monohydroperoxide, p-methane hydroperoxide, pinane hydroperoxide, and the like. Two or more of the organic peroxides may be used in combination. Among these, cumene hydroperoxide is preferably used in terms of curability of the dental polymerizable composition of the present embodiment.

The content of the organic peroxide in the dental polymerizable composition of the present embodiment is preferably 0.01% by mass or more and 5% by mass or less, and further preferably 0.1% by mass or more and 2% by mass or less. If the content of the organic peroxide in the dental polymerizable composition of the present embodiment is 0.01% by mass or more, the curability of the dental polymerizable composition of the present embodiment is further improved. If the content of the organic peroxide in the dental polymerizable composition of the present embodiment is 5% by mass or less, the working time of the dental polymerizable composition of the present embodiment is further increased.

[Thiourea Derivative]

An organic peroxide functions as a reducing agent for a chemical polymerization initiator.

Examples of the thiourea derivatives include ethylene thiourea, N-methylthiourea, N-ethylthiourea, N-propylthiourea, N-butylthiourea, N-lauryl thiourea, N-phenylthiourea, N-cyclohexylthiourea, N,N-dimethyl thiourea, N,N-diethylthiourea, N,N-dipropylthiourea, N,N-dibutylthiourea, N,N-dilauryl thiourea, N,N-diphenylthiourea, N,N-dicyclohexylthiourea, trimethylthiourea, tetramethyl thiourea, N-acetylthiourea, N-benzoyl thiourea, 1-allyl-3-(2-hydroxyethyl)-2-thiourea, 1-(2-tetrahydrofurfuryl)-2-thiourea, N-tert-butyl-N'-isopropylthiourea, 2-pyridylthiourea, and the like. Two or more of the thiourea derivatives may be used in combination. Among these, N-benzoyl thiourea is preferably used in terms of curability of the dental polymerizable composition of the present embodiment.

The content of the thiourea derivative in the dental polymerizable composition of the present embodiment is preferably 0.1% by mass or more and 5% by mass or less, and further preferably 0.1% by mass or more and 1% by mass or less. If the content of the thiourea derivative in the dental polymerizable composition of the present embodiment is 0.1% by mass or more, the curability of the dental polymerizable composition of the present embodiment is further improved. If the content of the thiourea derivative in the dental polymerizable composition of the present embodiment is 5% by mass or less, the solubility of the thiourea derivative in the dental polymerizable composition of the present embodiment to (meth)acrylate is further improved.

[Vanadium Compound]

A vanadium compound functions as a reducing agent for a chemical polymerization initiator.

Examples of the vanadium compounds include oxovanadium oxalate, vanadyl acetylacetonate, vanadium acetylacetonate, vanadyl stearate, vanadium naphthenate, vanadium benzoyl acetonate, and the like. Two or more of the vanadium compounds may be used in combination. Among these, vanadyl acetylacetonate is preferably used in terms of curability of the dental polymerizable composition of the present embodiment.

The content of the vanadium compound in the dental polymerizable composition of the present embodiment is preferably 0.001% by mass or more and 1% by mass or less, and further preferably 0.002% by mass or more and 0.1% by mass or less. If the content of the vanadium compound in the dental polymerizable composition of the present embodiment is 0.001% by mass or more, the curability of the dental polymerizable composition of the present embodiment is further improved. If the content of the vanadium compound in the dental polymerizable composition of the present embodiment is 1% by mass or less, the storage stability of the dental polymerizable composition of the present embodiment is further improved.

[β-diketone]

β-diketone is preferably a compound represented by the following general formula:

[Chemical Formula 1]

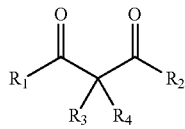

(wherein $R_1$ and $R_2$ are each independently an alkyl group or aryl group of 1 to 7 carbon atoms which may be substituted by a halogen atom, and $R_3$ and $R_4$ are each independently an alkyl group or aryl group of 1 to 6 carbon atoms which may be substituted by a hydrogen atom or a halogen atom, or a halogen atom, and $R_1$ and $R_3$, or $R_1$ and $R_2$ may form a ring structure.

Examples of the β-diketones include acetylacetone, 3,5-heptanedione, 1-phenyl-1,3-butanedione, 3-ethyl-2,4-pentanedione, dipivaloylmethane, 2,6-dimethyl-3,5-heptanedione, 3-methyl-2,4-pentanedione, 6-methyl-2,4-heptanedione, 3-methylnonane-2,4-dione, 1,3-cycloheptanedione, 2-acetylcyclopentanone, dimedone, 2-methyl-1,3-cyclopentanedione, 2-ethyl-1,3-cyclopentanedione, 4,4-dimethyl-1,3-cyclohexanedione, 5-methyl-1,3-cyclohexanedione, 2-methyl-1,3-cyclohexanedione, 1,3-cyclopentanedione, 2-acetylcyclohexanone, 3-chloroacetylacetone, trifluoroacetyl acetone, 1,1,5,5-tetrafluoro-2,4-pentanedione, hexafluoroacetylacetone, and the like. Two or more of the β-diketones may be used in combination. Among these, acetylacetone is preferably used in terms of storage stability of the dental polymerizable compositions of the present embodiment.

The content of the β-diketone in the dental polymerizable composition of the present embodiment is preferably 0.005% by mass or more and 5% by mass or less, and further preferably 0.01% by mass or more and 2.5% by mass or less. If the content of the β-diketone in the dental polymerizable composition of the present embodiment is 0.005% by mass or more, the storage stability of the dental polymerizable composition of the present embodiment is further improved. If the content of the β-diketone in the dental polymerizable composition of the present embodiment is 5% by mass or less, the curability of the dental polymerizable composition of the present embodiment is further improved.

The mass ratio of the β-diketone to the vanadium compound is preferably from 0.1 to 500, and further preferably from 0.5 to 300. If the mass ratio of the β-diketone to the vanadium compound is 0.1 or greater, the storage stability of the dental polymerizable composition is further improved. If the mass ratio of the β-diketone to the vanadium compound is 500 or less, the curability of the dental polymerizable composition of the present embodiment is further improved.

[Other Components]

The first agent may further contain a tertiary amine.

The tertiary amine functions as a reducing agent for a chemical polymerization initiator.

The tertiary amine may be either a tertiary aliphatic amine or a tertiary aromatic amine, but is preferably a tertiary aromatic amine, and particularly preferably an alkyl p-dialkylaminobenzoate.

Examples of the tertiary aliphatic amines include N,N-dimethylaminoethylmethacrylate, triethanolamine, and the like.

Examples of the alkyl p-dialkylaminobenzoate include methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate, propyl p-diethylaminobenzoate, and the like.

Examples of the tertiary aromatic amines other than alkyl p-dialkylaminobenzoate include 7-dimethylamino-4-methylcoumarin, N,N-dimethylaniline, N,N-dibenzylaniline, N,N-dimethyl-p-toluidine, N,N-diethyl-p-toluidine, N,N-bis(2-hydroxyethyl)-p-toluidine, N,N,2,4,6-pentamethylaniline, N,N,2,4-tetramethylaniline, N,N-diethyl-2,4,6-trimethylaniline, and the like.

The tertiary amine may be used alone or in combination with two or more tertiary amines.

The first agent and/or the second agent may further include a polymerization inhibitor, a photoinitiator, a filler, a chelating agent, and the like.

Examples of the polymerization inhibitors include dibutyl hydroxytoluene, 6-tert-butyl-2,4-xylenol, 2,6-di-tert-butyl-p-cresol, and the like. Two or more of the polymerization inhibitors may be used in combination.

Examples of the photopolymerization initiators include camphorquinone, phenylbis (2,4,6-trimethylbenzoyl) phosphine oxide, 2,4,6-trimethylbenzoyl diphenylphosphine, benzyl ketal, diacetyl ketal, benzyl dimethyl ketal, benzyl bis (2-methoxyethyl) ketal, 4,4'-dimethyl (benzyl dimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, benzoin isopropyl ether, benzoin isobutyl ether, benzophenone, bis(4-dimethylaminophenyl)ketone, 4,4'-bis(diethylamino)benzophenone, and the like. Two or more of the photopolymerization initiators may be used in combination.

Examples of the fillers include anhydrous silicic acid powder, fumed silica, alumina powder, glass powder (for example, barium glass powder, fluoroaluminosilicate glass powder), and the like. Two or more of the fillers may be used in combination.

The filler may be treated with a surface treatment agent such as a silane coupling agent.

The content of the filler in the dental polymerizable composition of the present embodiment is preferably 4% by mass or more and 90% by mass or less, and further preferably 15% by mass or more and 80% by mass or less. If the content of the filler in the dental polymerizable composition of the present embodiment is 4% by mass or more, the mechanical strength of the cured product of the dental polymerizable composition in the present embodiment is further improved. If the content of the filler in the dental polymerizable composition of the present embodiment is 90% by mass or less, the workability of the dental polymerizable composition of the present embodiment is further improved.

Examples of the chelating agents include edetate such as disodium dihydrogen ethylenediaminetetraacetate, ethylenediaminetetraacetic acid, trisodium ethylenediaminetetraacetate, tetrasodium ethylenediaminetetraacetate, and the like; phosphonates such as trans-1,2-cyclohexanediaminetetraacetic acid, hydroxyethyl ethylenediamine triacetate, diethylenetriamine pentaacetate, ethylenediamine tetramethylene phosphonic acid, nitrilotrismethylene phosphonic acid, and the like; phytic acid, oxalic acid, polyaspartic acid, polyglutamic acid, polyphosphoric acid, metaphosphoric acid, pyrophosphoric acid, hexametaphosphoric acid, phosphoric acid, citric acid, lactic acid, alanine, tannin, dihydroxyethylglycine, gluconic acid, salicylic acid, succinic acid, malic acid, tartaric acid, their salts, and the like. Two or more of the chelating agents may be used in combination.

EXAMPLES

Hereinafter, examples of the present invention will be described, but the present invention is not limited to the examples.

Examples 1 to 10, Comparative Example 1

(Preparation of Paste 1)

Paste 1 was prepared by mixing methacrylate not having an acid group, a vanadium compound, @-diketone, a thiourea derivative, a filler, a tertiary amine, a photopolymerization initiator, and a polymerization inhibitor in the blends [% by mass] indicated in Table 1.

(Preparation of Paste 2)

Paste 2 was prepared by mixing methacrylate not having an acid group, methacrylate having an acid group, an organic peroxide, a filler, a chelating agent, and a polymerization inhibitor in the blends [% by mass] indicated in Table 1.

The meanings of abbreviations in Table 1 are as follows.
GDMA: 2-hydroxy-1,3-dimethacryloyloxypropane
UDMA: di-2-methacryloyloxyethyl-2,2,4-trimethylhexamethylene dicarbamate
VAA: vanadyl acetylacetonate
acac: acetylacetone
NBTU: N-benzoyl thiourea
Silica powder 1: RAF1000 (manufactured by TATSUMORI LTD.)
Silica Powder 2: Aeroil R812 (hydrophobic fumed silica) (manufactured by Aerosol Japan)
EPA: ethyl p-dimethylaminobenzoate
CQ: camphorquinone
IA: 6-tert-butyl-2,4-xylenol
MDP: 10-methacryloyloxydecyldihydrogenphosphate
CHP: cumene hydroperoxide
EDTA salt: disodium dihydrogen ethylenediamine tetraacetate dihydrate The storage stability of pastes 1 and 2 (two-component dental polymerizable composition) was then evaluated.

[Storage Stability]

Accelerated testing was performed to evaluate the storage stability of the two-component dental polymerizable composition. Specifically, the pastes 1 and 2 were stored at 60° C. for 10 days, and the pastes 1 and 2 before and after storage were then kneaded at a mass ratio of 1.3:1 to determine the curing time. Here, after the acrylic ring having an inner diameter of 8 mm and a thickness of 2 mm was filled with the pastes 1 and 2, the curing time was measured by measuring the temperature of the kneaded product of pastes 1 and 2 using an infrared radiation thermometer.

The evaluation criteria for determining storage stability are as follows.

Excellent: When the change of curing time before and after the storage is 60 seconds or less.

Good: When the change of curing time before and after the storage exceeds 60 seconds and 150 seconds or less.

Fail: When the change of curing time before and after the storage exceeds 150 seconds.

Table 1 indicates the evaluation results of the storage stability of the two-component dental polymerizable composition.

TABLE 1

| | | | Examples | | | | | |
|---|---|---|---|---|---|---|---|---|
| | | | 1 | 2 | 3 | 4 | 5 | 6 |
| Paste 1 | Methacrylate free of acid group | GDMA | 14.5 | 14.5 | 14.5 | 14.5 | 14.5 | 15.0 |
| | | UDMA | 14.5 | 14.5 | 14.5 | 14.5 | 14.5 | 15.0 |
| | Vanadium compound | VAA | 0.024 | 0.024 | 0.024 | 0.018 | 0.012 | 0.006 |
| | β-$_{diketone}$ | acac | 0.9 | | | 0.7 | 0.45 | 0.23 |
| | | 3,5-heptanedione | | 0.9 | | | | |
| | | 1-phenyl-1,3-butanedione | | | 0.9 | | | |

TABLE 1-continued

|  |  |  | | | | | | |
|---|---|---|---|---|---|---|---|---|
|  | Thiourea derivative | NBTU | 0.5 | 0.5 | 0.5 | 0.5 | 0.5 | 0.5 |
|  | Fillers | Silica particles 1 | 63.5 | 63.5 | 63.5 | 63.5 | 63.5 | 63.5 |
|  |  | Silica particles 2 | 6.0 | 6.0 | 6.0 | 6.0 | 6.0 | 6.0 |
|  | Tertiary amine | EPA | 0.2 | 0.2 | 0.2 | 0.2 | 0.2 | 0.2 |
|  | Photopolymerization initiator | CQ | 0.1 | 0.1 | 0.1 | 0.1 | 0.1 | 0.1 |
|  | Polymerization inhibitor | IA | 0.05 | 0.05 | 0.05 | 0.05 | 0.05 | 0.05 |
|  | Total |  | 100 | 100 | 100 | 100 | 100 | 100 |
| Paste 2 | Methacrylate free of acid group | GDMA | 7.0 | 7.0 | 7.0 | 7.0 | 7.0 | 7.0 |
|  |  | UDMA | 37.0 | 37.0 | 37.0 | 37.0 | 37.0 | 37.0 |
|  | Methacrylate having acid group | MDP | 3.0 | 3.0 | 3.0 | 3.0 | 3.0 | 3.0 |
|  | Organic peroxide | CHP | 1.0 | 1.0 | 1.0 | 1.0 | 1.0 | 1.0 |
|  | Filler | Silica particles 1 | 45.0 | 45.0 | 45.0 | 45.0 | 45.0 | 45.0 |
|  |  | Silica particles 2 | 7.0 | 7.0 | 7.0 | 7.0 | 7.0 | 7.0 |
|  | Chelating agent | EDTA salt | 0.2 | 0.2 | 0.2 | 0.2 | 0.2 | 0.2 |
|  | Polymerization inhibitor | IA | 0.05 | 0.05 | 0.05 | 0.05 | 0.05 | 0.05 |
|  | Total |  | 100 | 100 | 100 | 100 | 100 | 100 |
| Storage stability | Curing time before storage |  | 2'04" | 1'45" | 1'39" | 1'58" | 2'50" | 4'19" |
|  | Curing time after storage |  | 2'02" | 4'00" | 2'14" | 2'10" | 3'16" | 5'37" |
|  | Evaluation criteria |  | Excellent | Good | Excellent | Excellent | Excellent | Good |

|  |  |  | Examples | | | | Comparative Example |
|---|---|---|---|---|---|---|---|
|  |  |  | 7 | 8 | 9 | 10 | 1 |
| Paste 1 | Methacrylate free of acid group | GDMA | 15.0 | 15.0 | 15.0 | 14.5 | 15.0 |
|  |  | UDMA | 15.0 | 15.0 | 15.0 | 14.5 | 15.0 |
|  | Vanadium compound | VAA | 0.024 | 0.024 | 0.024 | 0.006 | 0.024 |
|  | β-diketone | acac | 0.01 | 0.045 | 0.1 | 0.9 |  |
|  |  | 3,5-heptanedione |  |  |  |  |  |
|  |  | 1-phenyl-1,3-butanedione |  |  |  |  |  |
|  | Thiourea derivative | NBTU | 0.5 | 0.5 | 0.5 | 0.5 | 0.5 |
|  | Fillers | Silica particles 1 | 63.5 | 63.5 | 63.5 | 63.5 | 63.5 |
|  |  | Silica particles 2 | 6.0 | 6.0 | 6.0 | 6.0 | 6.0 |
|  | Tertiary amine | EPA | 0.2 | 0.2 | 0.2 | 0.2 | 0.2 |
|  | Photopolymerization initiator | CQ | 0.1 | 0.1 | 0.1 | 0.1 | 0.1 |
|  | Polymerization inhibitor | IA | 0.05 | 0.05 | 0.05 | 0.05 | 0.05 |
|  | Total |  | 100 | 100 | 100 | 100 | 100 |
| Paste 2 | Methacrylate free of acid group | GDMA | 7.0 | 7.0 | 7.0 | 7.0 | 7.0 |
|  |  | UDMA | 37.0 | 37.0 | 37.0 | 37.0 | 37.0 |
|  | Methacrylate having acid group | MDP | 3.0 | 3.0 | 3.0 | 3.0 | 3.0 |
|  | Organic peroxide | CHP | 1.0 | 1.0 | 1.0 | 1.0 | 1.0 |
|  | Filler | Silica particles 1 | 45.0 | 45.0 | 45.0 | 45.0 | 45.0 |
|  |  | Silica particles 2 | 7.0 | 7.0 | 7.0 | 7.0 | 7.0 |
|  | Chelating agent | EDTA salt | 0.2 | 0.2 | 0.2 | 0.2 | 0.2 |
|  | Polymerization inhibitor | IA | 0.05 | 0.05 | 0.05 | 0.05 | 0.05 |
|  | Total |  | 100 | 100 | 100 | 100 | 100 |
| Storage stability | Curing time before storage |  | 2'10" | 2'17" | 2'03" | 3'26" | 2'29" |
|  | Curing time after storage |  | 4'13" | 3'52" | 3'33" | 3'49" | 5'17" |
|  | Evaluation criteria |  | Good | Good | Good | Excellent | Fail |

From Table 1, it can be seen that the two-component dental polymerizable compositions in Examples 1 to 10 exhibits high storage stability.

In contrast, the two-component dental polymerizable composition in Comparative Example 1 exhibits low storage stability because the paste 1 does not contain the β-diketone.

The present application is based on and claims priority of Patent Application No. 2019-164833, filed Sep. 10, 2019 with the Japan Patent Office, and the entire contents of Japanese Patent Application No. 2019-164833 are hereby incorporated by reference.

The invention claimed is:

1. A dental polymerizable composition comprising:
   a first agent containing a (meth)acrylate, a thiourea derivative, vanadyl acetylacetonate, and a β-diketone; and
   a second agent containing a (meth)acrylate and an organic peroxide, wherein
   the β-diketone is either acetylacetone, 1-phenyl-1,3-butanedione, or both,
   a content of the β-diketone in the first agent is 0.45% by mass or more and 0.9% by mass or less, and a content of vanadyl acetylacetonate in the first agent is 0.012% by mass or more and 0.024% by mass or less.

2. The dental polymerizable composition according to claim 1, wherein the β-diketone is acetylacetone.

* * * * *